United States Patent [19]

Oberhardt et al.

[11] 4,307,070
[45] Dec. 22, 1981

[54] METHODS AND APPARATUSES FOR PERFORMING IMMUNOASSAYS

[75] Inventors: Bruce J. Oberhardt, Katonah; Leonard Ornstein, White Plains, both of N.Y.

[73] Assignee: Technicon Instruments Corporation, Tarrytown, N.Y.

[21] Appl. No.: 8,202

[22] Filed: Jan. 31, 1979

[51] Int. Cl.³ .......................... G01N 33/48; G01T 1/00
[52] U.S. Cl. ...................................... 424/1; 23/230 B; 424/12
[58] Field of Search ............................. 424/1, 12, 1.5; 23/230 B

[56] References Cited

U.S. PATENT DOCUMENTS

| | | | |
|---|---|---|---|
| 3,966,897 | 6/1976 | Renn et al. | 424/1.5 |
| 4,152,242 | 5/1979 | Makonkawkeyoon | 424/12 |
| 4,198,389 | 4/1980 | Wadsworth | 424/12 |

Primary Examiner—Christine M. Nucker
Attorney, Agent, or Firm—S. P. Tedesco

[57] ABSTRACT

Methods and apparatuses are featured for preconcentrating immunological reactants prior to their contact and reaction to enhance the rate of reaction for separating reacted and unreacted reactants and, also, to increase the sensitivity at the detector-measuring system. The preconcentration of the reactants finds particular use in immunoassays, where very often an immunospecies is very dilute causing a time consuming and/or insensitive assay. The preconcentration and separation are accomplished within the reaction medium resulting in a simplified and compact apparatus.

14 Claims, 12 Drawing Figures

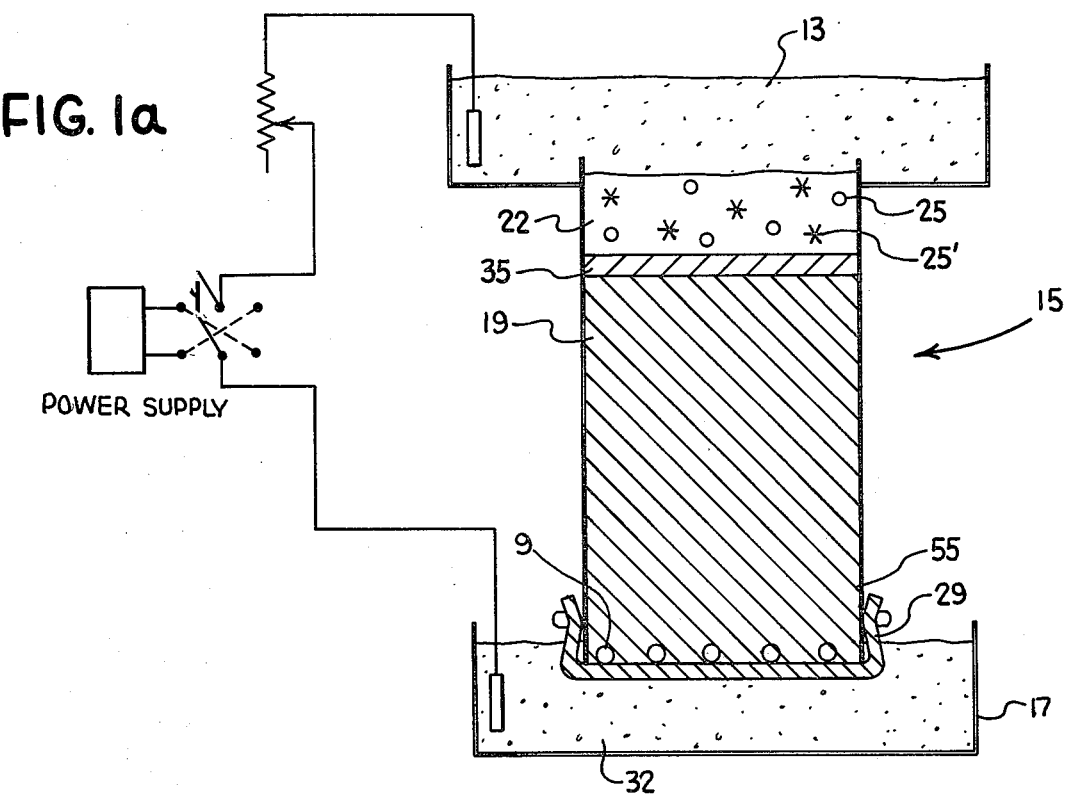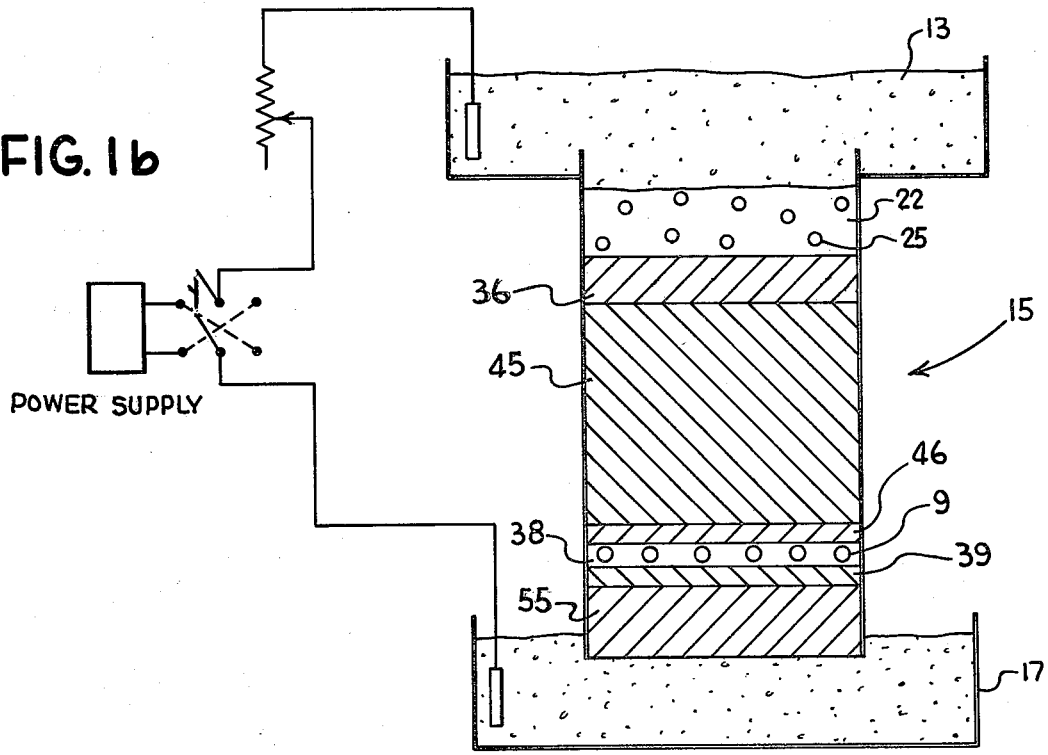

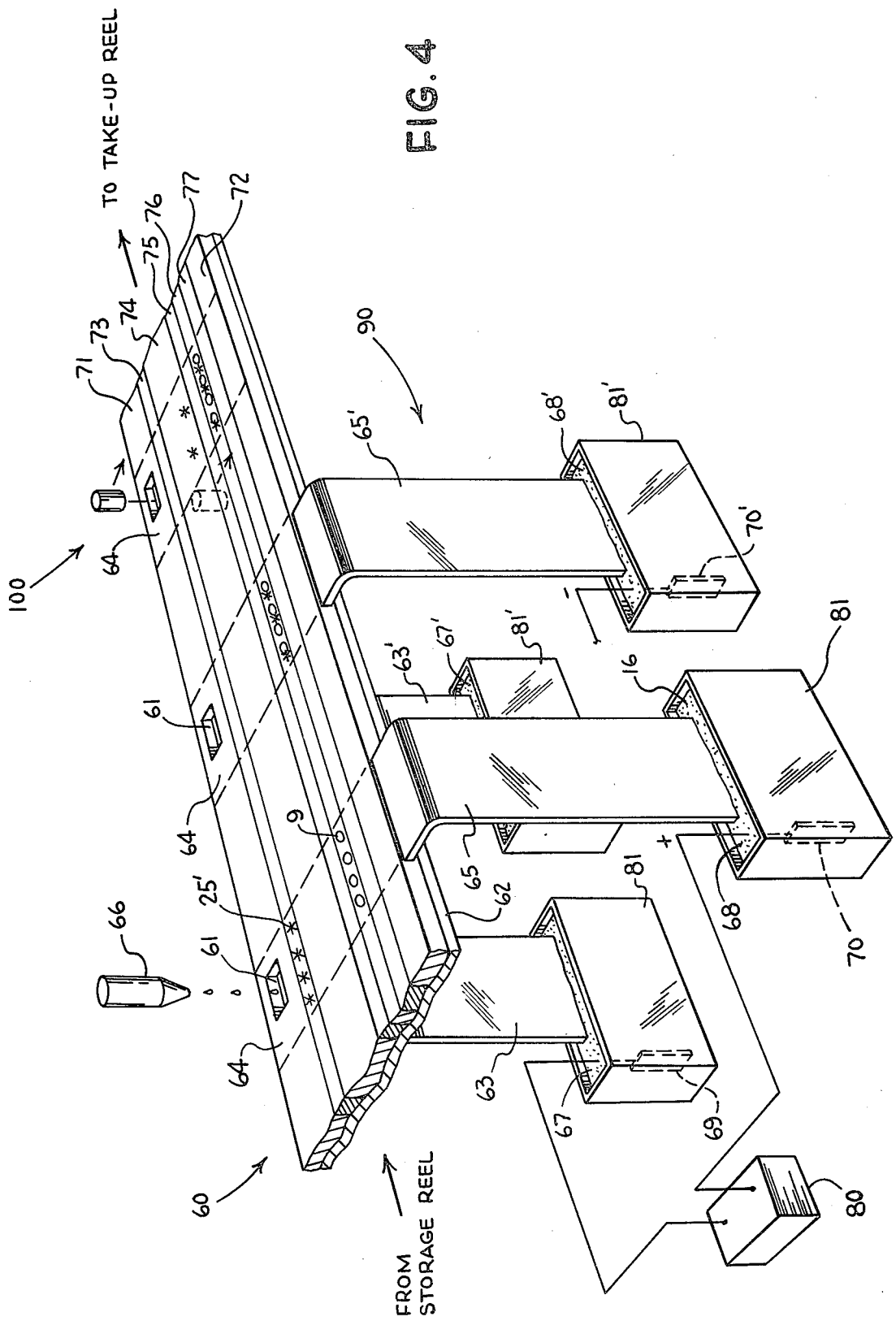

METHODS AND APPARATUSES FOR PERFORMING IMMUNOASSAYS

FIELD OF INVENTION

The invention pertains to methods and apparatuses for conducting an immunological reaction in a rapid and cost effective manner, by means of preconcentrating the reactants.

BACKGROUND OF THE INVENTION AND PRIOR ART

In the field of immunoassaying, reacting species are often very dilute, which results in assays that require an extended incubation time to provide an observable result and which are insensitive.

For example, for the assay of some serum constituents such as traces of hormones (e.g., ACTH), the concentration is so low that the reaction with an approximately stoichiometric equivalent of specific antibody may take more than 24 hours to complete. (See, e.g., *Radioimmunoassay & Related Techniques Methodology & Clinical Application* by Thorell & Larson, published by C. V. Mosby Co., St. Louis, 1978, pp. 144, 186, 198, 200).

If the concentration of antibody and antigen were to be increased by 300 times each, the bimolecular reaction rate between them will be speeded by $300 \times 300 = 90,000$ times, which results in reducing a 24 hour reaction rate to less than 1 second.

When the label used in an immunoassay is a chromophore, fluorophore, spin label, etc., the sensitivity with which it can be assayed is directly proportional to the concentration of the label in the final assay volume (when the detector system has been scaled to that volume). Therefore, these methods, which concentrate the immunoreactants to speed the reaction, also provide a substantial increase in assay sensitivity.

Despite the fact that preconcentrating has been recognized as desirable, to date there is no convenient means of accomplishing this result. Reactants can be preconcentrated by centrifugation, but this technique is not entirely satisfactory. In the first instance, the preconcentrated reactants often must be partly rediluted when they are removed from the centrifuge for reaction purposes. Secondly, this procedure usually requires expensive equipment. Thirdly, the procedure is inordinately time consuming. This is especially so for species of low molecular weight such as small antigens like angiotensin and haptens.

The invention achieves preconcentration of at least one reactant of the reaction in the very medium in which the reaction is accomplished. This eliminates the aforementioned drawback of redilution. In addition, the invention causes the reactants to preconcentrate at concentrations many times greater than generally achievable in prior art methods as applied to immunoassays. Furthermore, the invention seeks to achieve all these objectives at low cost, and in a rapid manner.

An assaying technique of the prior art features the reaction of immunoreactants, antigen (or hapten) on one hand, and antibody on the other, within a localized zone of a gel medium. The test substance is caused to migrate by electrophoresis through the gel into reactive contact with the immobilized reactant. After equilibration takes place, the unreacted or unbound substances are separated by further electrophoresis away from the immobilized reactant. Such a system as described above, may be seen with reference to U.S. Pat. No. 3,966,897. This invention, however, does not teach how the reactants may be preconcentrated within the gel reaction medium.

Another technique which has been known to concentrate constituents of a fluid sample within a medium is known as discelectrophoresis. This method was invented by L. Ornstein, one of the present inventors, and is described in U.S. Pat. No. 3,384,564, issued May 21, 1968. This technique features developing a discontinuous electric field across a gel medium. Different constituents of a fluid sample with the same sign charge will initially migrate through the gel at different speeds. Each constituent will rapidly concentrate into a narrow band, the process terminating in a steady state with all the same sign of charge constituents migrating at the same speed with a distinct order in the gel.

While this technique has been used to separate and concentrate components of a sample, it never has been used or suggested as a method for bringing together two immunological species at high concentration for performing a controlled reaction.

The present invention is generally distinguished from the prior immunoassay art by means of its selective sieving of the constituents of a reaction in order to concentrate them. In the prior immunoassay art, as molecules of the reactants migrate through a medium in an electrophoretic field, they also tend to randomly diffuse in every direction. Consequently, a dilute substance traveling through a liquid or gel medium will tend to further dilute. This is so, because some reactant molecules will be diffusing backwardly even while the overall mass of substance is moving forwardly through the medium in an electric field. In the prior art, the ultimate potential for achieving extremely rapid reaction rates is never fully realized. This is because the reactants are not brought together in concentrated form.

In the invention, a gel or non-convecting medium is selected to eliminate non-random convective migration of the reactant molecules. One of the reactant species is caused to migrate through the medium towards a concentration or barrier zone which is permeable to small ions but impermeable to the reactant species. This concentration or barrier zone does not allow further migration of the arriving reactants. The continuing electrophoretic force will then cause the molecules of the substance to concentrate in a narrow zone very close to the barrier, such that the reactants will become very concentrated within a very small volume. If the other reactant species is already concentrated and disposed within the concentration zone, then the arrival and concentration of the complementing reactant wil initiate a very rapid reaction. In another embodiment, the second reactive species can be added to the system after the first has concentrated. It too will migrate towards the barrier and concentrate in the same region as the first. In the case of some immunoreactions, it may be required that subsequent to the reaction, bound and unbound reactants be separated. This may be achieved, for example, by reversal of the direction of the electrophoretic force. In this case, the reacted species can be arranged to be immobilized in the medium, because its size has been increased as a result of the reaction and it cannot migrate in the medium. The molecules of the unreacted species can, however, move out of the reaction zone as rapidly as they moved in. The determination of the unknown reactant in the sample can then be measured within the medium by known procedures.

SUMMARY OF THE INVENTION

The invention relates to methods and apparatuses for conducting chemical or immunological reactions within a medium, wherein at least one component of the reaction is preconcentrated within the reaction medium before the reaction has occurred. The medium is one featuring a limited convection characteristic and a semipermeable barrier for concentration. In other words, the medium allows for the movement of reactants through the medium in a precisely controlled and selective manner. The control of the migration and selective sieving of the reactants in the medium are used to concentrate them as they are forced to relatively move towards reactive contact with each other. In keeping with the teachings of this invention, a gel is a medium permitting no convection and a highly viscous liquid is a medium having very limited convection.

The method of the invention features the steps of: (a) migrating an immunoreactive constituent of a fluid sample within a medium; (b) concentrating the constituent within a portion of the medium; and (c) reacting the concentrated constituent with a reactant contained within the portion of the medium. The migration of the constituent is electrically induced.

It is an object of the invention to provide a way of performing a rapid reaction with initially dilute reactants.

It is another object of this invention to preconcentrate and react one or more reactants within the same medium.

It is still another object of the invention to provide a low cost, rapid way to perform immunoassays.

It is a further object of this invention to provide methods and apparatuses for performing a more sensitive assay.

These and other objects of this invention will be better understood and become more apparent with reference to the following detailed description taken in conjunction with the accompanying drawings in which:

BRIEF DESCRIPTION OF THE DRAWINGS

FIGS. 1a and 1b are schematic views of other embodiments of the apparatus shown in FIG. 1;

FIG. 4 is a schematic perspective view of an automated system.

DETAILED DESCRIPTION

Figure 1:
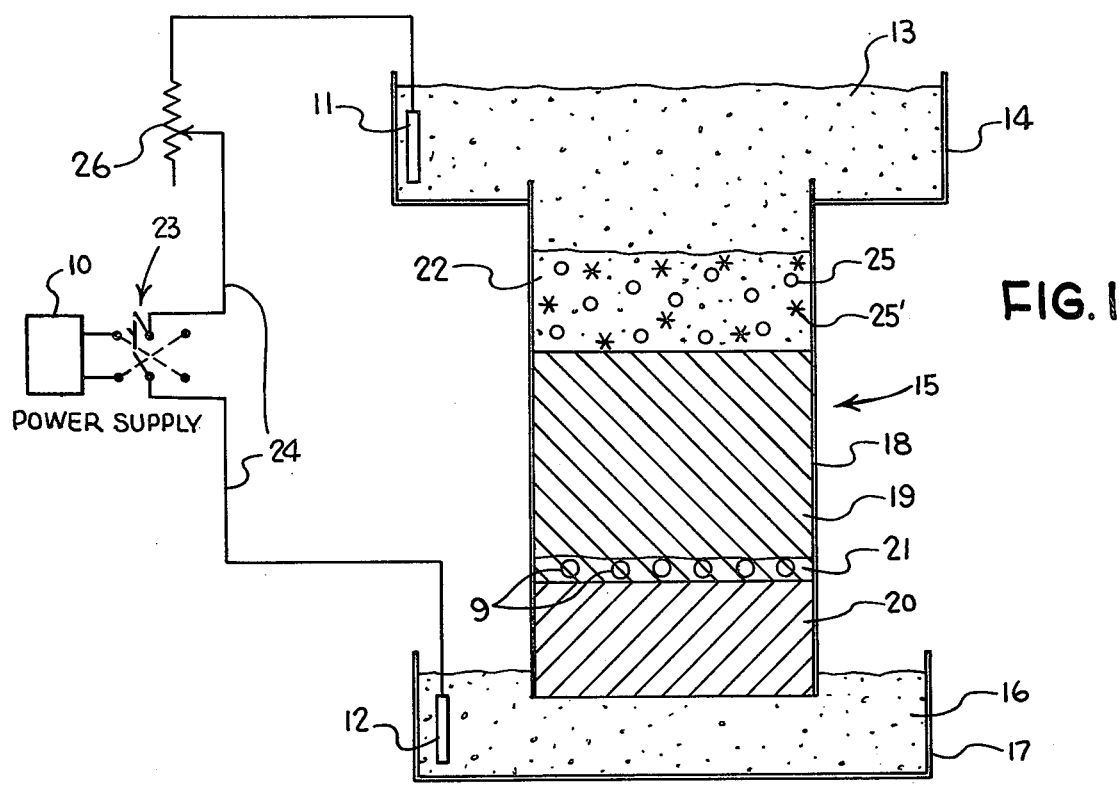
FIG. 1 is a schematic sectional view of one embodiment of the invention.

Referring to FIG. 1, one embodiment of the invention is shown in a sectional schematic view. A source 10 of D.C. current can apply a potential between electrodes 11 and 12, respectively. Electrode 11 is submerged within a buffer solution 13 contained in an upper compartment 14 of container 15. Electrode 12 is submerged within a buffer solution 16 contained in a lower compartment 17 of container 15. A mid-compartment 18 of container 15 acts as an electrical bridge between electrodes 11 and 12. The mid-compartment 18 contains two gel layers 19 and 20, respectively. The upper layer 19 is a large pore-size gel, and the lower layer 20 is a small pore-size gel.

If an immunoassay is to be performed for a particular antigen 25 (Ag), a thin layer 21 of a concentrated known amount of antibodies 9 (Ab) reactive toward the particular antigen 25 (Ag) is disposed between gel layers 19 and 20. The sample 22 containing an unknown amount of the antigen 25 (Ag) to be assayed and a known amount of labelled antigens 25' (Ag*), is deposited on top of gel layer 19 within buffer solution 13, as illustrated. The sample 22 may be mixed with a non-ionic substance such as sucrose in 20 to 40% concentration for the purpose of increasing the density of the antigen sample 22 to permit easy layering under the buffer 13.

The pore size of the small pore gel 20 is selected so that antibodies (Ab) and antigens (Ag+Ag*) cannot penetrate this layer. This will trap and concentrate the reactants in a thin layer at the juncture between layers 19 and 20. The immunoreaction will, therefore, be confined within this narrow zone layer 21. Because the reactants will be concentrated when they react in layer 21, a very rapid reaction will result.

When the process is to begin, a switch 23 is closed in lines 24, thus impressing a voltage between electrodes 11 and 12, as aforementioned. With the appropriate choice of pH and electrical polarity, this will cause an electrophoretic migration of the antigens 25 and 25' in sample 22 towards the antibody layer 21. This invention applies only to those pairs of immunoreactants where at least one is, or can be made, ionic and if both are ionic, pairs are of like sign of charge and mobile in an appropriate pH range of approximately 3.0 to 10.0.

Figures 2A, 2B, 2C, 2D:
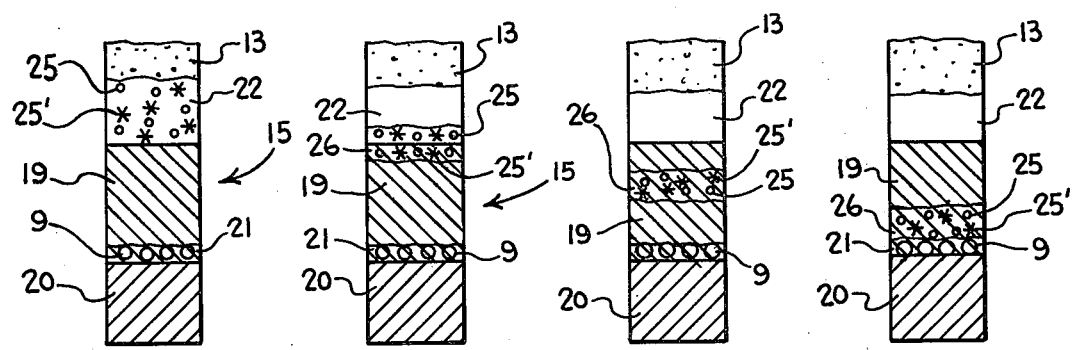
FIGS. 2a-2g are schematic sequential views of the operation of the apparatus depicted in FIG. 1.

FIGS. 2a through 2g depict in schematic sequence various stages of the progress of the electrophoretic migration being performed in the apparatus of FIG. 1. FIG. 2a shows the first stage of the migration with labelled 25' (Ag*) and unlabelled antigens 25 (Ag) in diluted form within sample 22 deposited on top of gel layer 19.

In FIG. 2b, the antigens 25 and 25' undergo a slight preconcentration as the voltage is impressed between electrodes 11 and 12. This slight preconcentration is due to the fact that the antigens are now entering gel medium 19 which slightly retards the rate of migration. The antigens 25 and 25' now form a slightly preconcentrated band 26.

FIG. 2c shows the next stage, prior to the immunoreaction where the slightly preconcentrated band of antigens 26 is beginning its migration through the large pore-size gel 19.

During this time, the concentrated antibodies 9 (Ab) in layer 21, if not immobilized but of same sign of charge as the antigens 25 and 25', may also have been migrating towards gel layer 20 forming an even more concentrated layer at the interface of elements 20 and 21.

Figures 2E, 2F, 2G, 3:
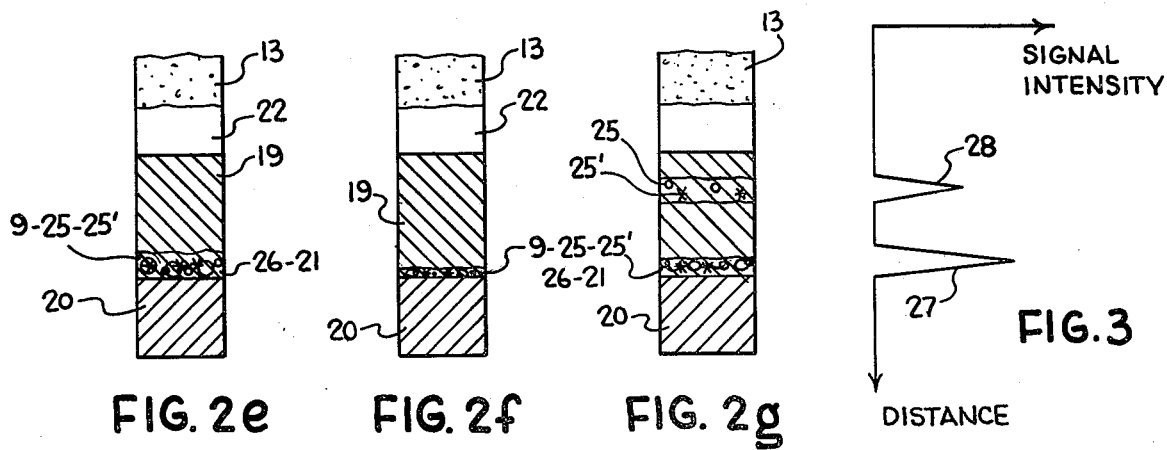
FIG. 3 is a schematic diagram of the reaction signals obtained from the operation of the apparatus of FIG. 1 in accordance with the method shown in FIGS. 2a-2g.

FIG. 2d shows the band of antigens 26 having migrated into the concentration zone above gel layer 20. At this stage in the assay procedure, the current is maintained until the band 26 becomes extremely concentrated and merges with the antibodies 9 in layer 21 (FIG. 2e). The voltage is then turned off via switch 23 of FIG. 1, as shown in FIG. 2f. The concentrated antigens (Ag and Ag*) are now allowed to react with the concentrated antibodies (Ab) via the process of "competitive binding." After rapid equilibration has take place, a reverse voltage is impressed on electrodes 11 and 12 via switch 23 to cause a reverse migration (separation) of any unbound antigens (25 and 25') as shown in FIG. 2g.

FIG. 3 shows a graph of the detector signal strength along the length of mid-portion 15 generated by the label of antigen 25' (Ag*).

The amount of antigens (Ag) in the original sample 22 is calculated in the standard manner by measuring the labelled antigen 25' (Ag*) in either the bound portion 27 and/or the unbound portion 28 of the reaction, as shown in FIG. 3.

The label used to tag the antigen 25' can be any one of a number of well-known substances such as fluorescent, chemiluminescent, enzyme or radioactive reagents, etc. These substances will provide a observable or measurable signal as per FIG. 3.

If layer 21 is absent, the antibodies 9 (Ab) may be concentrated in a similar fashion to that of the antigens, prior to the introduction of the sample 22. This is accomplished by introducing a dilute solution of antibodies 9 to the buffer solution 13 prior to the assay, and impressing the voltage between electrodes 11 and 12. The antibodies (Ab) will then migrate through gel 19 in a similar fashion as shown for the antigen in FIGS. 2b through 2d. When the antibodies (Ab) reach the top surface of the small pore gel 20, they will not be able to migrate any further and will become extremely concentrated in a layer disposed within the very bottom of layer 19.

Because of the added time needed for preconcentrating the antibodies by this latter method, the prior preconcentration method using layer 21 may be preferred.

The modified system described above can be further modified as follows:

FIG. 1a shows this modification, wherein a membrane 29 can be placed across the bottom of gel 19 in an apparatus similar to that shown for FIG. 1. The membrane 29 is meant as a replacement for gel 20. The gel 19 is a large pore-size gel which allows the passage of both antigens 25 and 25' (Ag+Ag*) and antibodies 9 (Ab). Membrane 29 allows the passage of small ions but does not allow for the passage of antigens 25 and 25' (Ag+Ag*) or antibodies 9 (Ab). Therefore, when electrophoretic migration of the antibodies 9 (Ab) is initiated prior to the assay, the antibodies 9 will be concentrated in a layer against the membrane 29 at the very bottom of gel 19.

The assay for antigens 25 (Ag) is performed in a similar manner to that shown in FIGS. 2a–2g.

FIG. 1b illustrates still another embodiment of the apparatus depicted in FIG. 1. The mid-compartment 15 now contains two separate large pore-size gel layers 45 and 55, respectively, two intermediate pore-size gels or membranes 36 and 46, respectively, a layer 38 of antibodies 9 and small pore-size gel or membrane 39.

The antigen containing sample 22 is layered under the buffer solution 13 as before, and deposits on top of layer 36, as shown. When the voltage is impressed, the antigens 25 and 25' of sample 22 begin to migrate through the gel layer 36. The function of this intermediate pore-size gel layer 36 is to be impermeable to large proteins in the sample 22 which will have migrated along with antigens 25 and 25'. Such large proteins may be substances such a albumin or gamma globulins. These substances are stopped before they reach the vicinity of the concentration zone by the first intermediate layer 36, so that they cannot interfere with the assay. The second intermediate membrane or gel layer 46 has as its purpose the entrapment of antibodies 9 within the layer 38. The antibodies remain within this layer 38 because they can neither move from layer 38 upwardly into the intermediate layer 46 nor downwardly into small pore-size gel or membrane layer 39. Thus, the application of current in either direction will not cause the antibodies to migrate from the concentration zone (layer 38). This embodiment functions in like fashion to the embodiment depicted in FIG. 1a, in that the antigens 25 and 25' will be greatly concentrated above impermeable membrane or gel layer 39, where they merge with antibody layer 38 and react. On reversal of current, unreacted labelled antigen 25' moves back into layer 55 which is free of sample substances which might interfere with detection and measurement.

Referring to FIG. 4, an automated system featuring a continuous tape 60 of gel materials is dispensed from a storage reel (not shown) towards a take-up reel (not shown). The tape 60 may have a supportive plastic backing 62 as shown. The tape 60 is stored in dehydrated form, and is rehydrated when dispensed from the storage reel by contact with a wetting wick (not shown). The storage of the tape in dehydrated form allows for the predeposit of labelled antigens (Ag*) and antibodies (Ab) in the tape. Thus, only the sample need be added to the system to perform an assay. Discrete sections 64 of said tape 60 are periodically indexed in seriatim past a pair of wicks 63 and 65, which are respectively in fluid contact with a pair of wells 81 containing buffer solutions 67 and 68; and electrodes 69 and 70, respectively. Each section 64 of tape 60 contains all the components for one complete assay. This apparatus is similar to that shown in FIG. 1b with the gel material being presented in flat continuous tape form to provide an automatic series of tests. A sample dispenser 66 is disposed above the tape 60 and periodically dispenses a sample into a well 61 in each section 64 as each section 64 is moved into fluid continuity with adjacent wicks 63 and 65. Each sample will permeate end layer 71 of tape 60. The power supply 80, establishes an electric field via wells 81 and wicks 63 and 65 across the tape 60 along the length of the section 64 disposed between wicks 63 and 65. The electric field will cause the sample in end layer 71 of tape 60 to move across the tape section 64 towards the other end layer 72 of the tape 60 by means of electrophoretic migration. Constituents within the tape are deposited below the surface of the tape and therefore migrate within the tape so as to eliminate surface effects and "spill over."

As the sample traverses across the tape section 64, it encounters a gel layer 73 designed to exclude large molecular components, such as albumin and gamma globulins, and which also contains a labelled constituent 25' (Ag*) equivalent to the constituent (Ag) to be determined in the sample. The labelled and sample constituents (Ag* and Ag) will migrate into a large pore-size gel in a mid-layer 74, and then subsequently into layers 75 and 76. Layer 76 contains a complementing immunospecies 9 (Ab) to the labelled and sample constituents (Ag* and Ag). The (Ab) is trapped in layer 76 for reaction with these (Ag* and Ag) constituents. Gel layer 75 is permeable to antigens (Ag* and Ag) and small ions. Gel layer 76 is permeable only to smaller ions but not to antigen (Ag* or Ag) or antibody (Ab) molecules.

When the reaction of the constituents with the complementing immunospecies has occurred, the particular section 64 containing these reactants is indexed to a second station 90 having respective wells 81', buffer solutions 67' and 68', electrodes 69' (not shown) and 70', and wicks 63' and 65', respectively. This second station 90 impresses an electric field of reverse polarity across sections 64, such that any unbound Ag and Ag* will not migrate backwardly into layer 74. The section 64 will now be indexed past a readout station 100 comprising a scan detector to detect the amount of labelled constituent in layer 74 and/or layer 76. Each section 64, in turn, will be indexed past the various dispensing, migrating, and readout stations. The stations are arranged to provide a high throughput. However, it is obvious that several of the processing stations can be combined with some sacrifice of throughput.

All of the embodiments of this invention seek to perform a concentration of one or more of the constituents of a reaction during the process of one or more of the constituents of a reaction during the process of electrophoretic migration through a limited or non-convecting medium. The concentrated constituents are brought into reactive contact within the same medium used for concentration, thus eliminating the need for redilution and transfer. All of the reactions are monitored within the same medium, which is convenient.

While the aforementioned description has mainly focused upon immunoassaying techniques, the same apparatuses can easily be utilized for many chemical reactions involving dilute reactants. In all the reactions contemplated by the invention, the constituents and immunospecies are either naturally ionic or can be made ionic by proper chemical treatment and choice of pH in solution.

The reactions can be monitored within the gel material by many standard fluorometric, photometric, colorimetric, etc., techniques.

Non-convecting mediums such as gels are preferred in the apparatus for controlling the migration of materials. Gels which can be used in the invention may be chosen from standard materials such as Sephadex, acrylamide, agarose, etc. Migration must be precisely controlled in order to obtain the very high concentrations which are sought. Preferably, these gels should also be translucent or transparent so that the reaction can be optically monitored within the gel.

It is also preferred to prevent diffusion or migration for those materials which are deposited prior to test within zones of the gel. For example, the predeposited antibodies disposed within a thin zone layer or on a membrane within the gel should be trapped in their prescribed zone. This may be accomplished by structural means such as surrounding these materials by small pore-size layers. Also, a slight electrophoretic potential may be maintained to hold them in place. In some cases, the antibodies may actually by covalently bound to a membrane or attached by bound latex, etc.

To summarize the invention, therefore, it is contemplated to preconcentrate at least one reactant or constituent during migration through a limited convecting medium, and further to react concentrated constituents and reactants within the same medium to provide both a rapid and sensitive reaction.

Having thus described our invention, what is sought to be protected by Letters Patent is presented by the following appended claims.

What is claimed is:

1. A method of assaying a constituent of a fluid sample within a porous medium in which said constituent is caused to migrate, said method comprising the steps of:
   (a) causing said constituent of said sample introduced into said medium to migrate within said medium;
   (b) limiting the migration of said constituent, so as to concentrate said constituent within a portion of said medium;
   (c) reacting said concentrated constituent with a reactant; and
   (d) monitoring the reaction between said constituent and said reactant.

2. The method of claim 1, wherein step (c) comprises the steps of:
   (e) causing said reactant to migrate within said medium; and
   (f) limiting the migration of said reactant, so as to concentrate said reactant within said portion of said medium.

3. The method of claim 1, wherein said constituent is a charged ion, and wherein step (a) is achieved by impressing an electric field along the length of said medium, so as to cause said charged ion constituent to migrate within said medium.

4. The method of claim 1, wherein step (b) includes the steps of:
   (e) allowing the migration of other constituents of said sample beyond said portion of said medium, so as to separate said constituent and said other constituents.

5. The method of claim 1, wherein said constituent is a charged ion, and wherein step (a) is achieved by impressing an electric field along the length of said medium to cause said charged ionic constituent to migrate within said medium, and further wherein step (c) includes the step of priorly immobilizing said reagent within said portion of said medium.

6. The method of claim 3, wherein said constituent and said reactant are ions of like sign of charge and comprising the further steps of:
   (e) initially introducing said constituent and said reagent sequentially into said medium;
   (f) maintaining said electric field until substantially all of said constituent and said reagent are concentrated within said portion of said medium; and
   (g) reversing said electric field following reaction of said constituent and said reagent to separate any unreacted constituent and any unreacted reagent from any reacted constituent.

7. The method of claim 6, wherein the monitoring step (d) of claim 1 comprises the step of:
   (i) measuring said separated reacted constituent to determine the amount of said constituent in said sample.

8. The method of claim 6, wherein the monitoring step (d) of claim 1 comprises the step of:
   (i) measuring said separated unreacted constituent to determine the amount of said constituent in said sample.

9. The method of claim 1, wherein said constituent is an immunospecies, said reactant is an immunospecies complement of said constituent, and said sample comprises an unknown amount of said constituent in combination with a known amount of tagged constituent, and wherein step (c) further comprises the step of:
   (e) competitively reacting to bind said known and unknown amounts of said constituent with a known amount of said reactant.

10. The method of claim 9, further comprising the step of:

(f) separating any unbound constituent from any bound constituent within said medium.

11. The method of claim 10, wherein the monitoring step (d) of claim 1 comprises the step of:
(g) measuring the bound constituent to determine said unknown amount of said constituent in said sample following separation of said bound and unbound constituents by step (f).

12. The method of claim 10, wherein the monitoring step (d) of claim 1 comprises the step of:
(g) measuring the unbound constituent to determine said unknown amount of said constituent in said sample following separation of said bound and unbound constituents by step (f).

13. The method of claim 2, wherein step (e) is effected following step (a) of claim 1.

14. The method of claim 2, wherein step (e) is effected prior to step (a) of claim 1.

* * * * *